(12) United States Patent
Athanasiou et al.

(10) Patent No.: US 9,931,444 B2
(45) Date of Patent: Apr. 3, 2018

(54) POLYMERIC COMPOSITE MATERIALS WITH ANTIMICROBIAL AND BIODEGRADABLE PROPERTIES AND USES THEREOF

(71) Applicant: FONDAZIONE ISTITUTO ITALIANO DI TECNOLOGIA, Genoa (IT)

(72) Inventors: Athanasia Athanasiou, Genoa (IT); Ilker S. Bayer, Genoa (IT); Ioannis Liakos, Genoa (IT); Loris Rizzello, Lecce (IT); Roberto Cingolani, Ceranesi (IT); Stefania Sabella, Lecce (IT); Pier Paolo Pompa, Lecce (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 14/384,591

(22) PCT Filed: Mar. 21, 2013

(86) PCT No.: PCT/IB2013/052245
§ 371 (c)(1),
(2) Date: Sep. 11, 2014

(87) PCT Pub. No.: WO2013/140362
PCT Pub. Date: Sep. 26, 2013

(65) Prior Publication Data
US 2015/0050234 A1    Feb. 19, 2015

(30) Foreign Application Priority Data
Mar. 21, 2012 (IT) .............. TO2012A0258

(51) Int. Cl.
*A61L 31/12* (2006.01)
*A61L 31/04* (2006.01)
(Continued)

(52) U.S. Cl.
CPC ............. *A61L 31/129* (2013.01); *A61L 15/46* (2013.01); *A61L 17/005* (2013.01);
(Continued)

(58) Field of Classification Search
None
See application file for complete search history.

(56) References Cited

U.S. PATENT DOCUMENTS 4,478,853 A * 10/1984 Chaussee ............... A61K 8/345
424/47
2006/0068013 A1    3/2006 DiTizio et al.
(Continued)

FOREIGN PATENT DOCUMENTS

CN          1192358      *  9/1998 ............. A61K 31/74
EP     0 532 275 A1       3/1993
(Continued)

OTHER PUBLICATIONS

Abstract, CN1192358 (1998).*
(Continued)

*Primary Examiner* — Bethany P Barham
*Assistant Examiner* — Barbara Frazier
(74) *Attorney, Agent, or Firm* — Merchant & Gould P.C.

(57) ABSTRACT

A composite material for the production of a medical device having an antiseptic action includes a matrix of alginate in which the complex of iodopovidone is dispersed. The composite material is used particularly for the production of films, micro-capsules, and suture threads with iodine controlled release.

5 Claims, 2 Drawing Sheets

(51) Int. Cl.
  *A61L 31/16* (2006.01)
  *A61L 27/54* (2006.01)
  *A61L 26/00* (2006.01)
  *A61L 24/00* (2006.01)
  *A61L 17/00* (2006.01)
  *A61L 15/46* (2006.01)

(52) U.S. Cl.
  CPC ....... *A61L 24/0015* (2013.01); *A61L 26/0066* (2013.01); *A61L 27/54* (2013.01); *A61L 31/042* (2013.01); *A61L 31/048* (2013.01); *A61L 31/16* (2013.01); *A61L 2300/202* (2013.01); *A61L 2300/404* (2013.01)

(56) References Cited

U.S. PATENT DOCUMENTS

2009/0221489 A1* 9/2009 Stenberg ................ A61K 9/006
　　　　　　　　　　　　　　　　　　　　　　　　514/4.8
2011/0171284 A1　　7/2011 Gilman et al.

FOREIGN PATENT DOCUMENTS

EP　　　1 258 256 A1　　11/2002
WO　　WO2013/078998　　*　6/2013　............... A61K 9/08

OTHER PUBLICATIONS

Machine translation, CN1192358 (1998).*
Yuan, Jinghua P., et al, "Effects of Polyethelene Glycol on Morphology, Thermomechanical Properties and Water Vapor Permeability of Cellulose Acetate Free Films", Pharmaceutical Technology, vol. 25, No. 10, pp. 62-74, 2001, (unedited version).

* cited by examiner

POLYMERIC COMPOSITE MATERIALS WITH ANTIMICROBIAL AND BIODEGRADABLE PROPERTIES AND USES THEREOF

This application is a National Stage Application of PCT/IB2013/052245, filed 21 Mar. 2013, which claims benefit of Serial No. TO2012A000258, filed 21 Mar. 2012 in Italy and which applications are incorporated herein by reference. To the extent appropriate, a claim of priority is made to each of the above disclosed applications.

BACKGROUND OF THE INVENTION

The present invention relates to a new antiseptic and biodegradable composite material, comprising the complex of povidone-iodine or iodopovidone (hereinbelow, PVPI) and alginate, and to medical devices produced with the use of the above-mentioned composite material.

The povidone-iodine complex is a water-soluble complex of iodine and polyvinylpyrrolidone widely used for its bactericide and fungicide properties. PVPI is known for its iodophor properties, i.e., as a substance acting as a vehicle or solubilizer for iodine and which is able to release into solution small amounts of free iodine, minimizing the toxicity thereof and preserving the moderate germicide activity of that element.

The most common form of the PVPI complex is its aqueous solution containing from 9% to 12% of available iodine (calculated on the anhydrous basis); aqueous solutions of PVPI are directly applied to open wounds or infected regions, a method commonly known as wound irrigation. While the low release of iodine from the PVPI complex into solution minimizes the toxicity of iodine for mammal cells, its quick absorption by open wounds during irrigation may cause severe toxicity problems, thus limiting the surgical applications thereof, particularly for repeated applications.

Besides its wide use as a skin antiseptic, PVPI is also used internally, for example on burns, large wounds, deep tissues, or mucosae.

In the dressing field, products for wound dressings are particularly available, using PVPI as an active ingredient in combination with polymeric substances, such as, for example, polyethylene glycol (PEG), such as, particularly the commercial product "INADINE" by Johnson & Johnson.

However, PEG has the drawback to be a synthetic, non-biodegradable polymer.

SUMMARY OF THE INVENTION

An object of the present invention is to provide new biodegradable materials suitable for a controlled release of PVPI.

Another object of the invention is to provide materials suitable for producing medical devices, and particularly of PVPI dispensing systems for use in the treatment of internal and external wounds, with PVPI controlled release properties.

A special object of the invention is to provide a medical device in the form of a self-supporting film for the PVPI release, useful as an antiseptic dressing for wounds.

Another object of the invention is to provide antiseptic filling systems, for internal and external use, of open wounds, particularly in the form of microcapsules.

A further object of the invention is to provide medical devices in the form of antiseptic and biodegradable surgical suture threads.

These objects are achieved by a composite material and medical devices composing an integral and integrant part of the present description.

Particularly, the invention provides composite materials consisting of, or comprising, a matrix of alginate in which the iodopovidone complex is dispersed.

The alginates used according to the invention are straight, non-branched polysaccharides, containing different proportions of β-D-mannuronic acid (M) and residues of α-L-guluronic acid (G). The M and G monomers are linked in the 1-4 position through glycosidic linkages, forming homopolymeric MM or GG blocks which are interspersed with heteropolymeric MG or GM blocks.

The molecular variability of these polymers depends on the source of seaweeds, from the tissues of which the alginates are extracted; among alginates, sodium alginate was widely considered as a non-toxic, natural material with properties of interest for drug dispensing systems. Since it is hydrophilic and biodegradable, it can be absorbed by the skin into bodily fluids without toxic effects, so as to be highly beneficial in the wound healing and cicatrization process.

Therefore, the composite material according to the invention, combining an alginate with PVPI, allows obtaining medical devices and PVPI dispensing systems achieving a synergic effect on wounds. Alginate provides a healing effect, while PVPI provides an antiseptic effect.

Particularly, it has been verified that the above-mentioned synergic effect can be achieved within specific relative weight ratios of alginate and PVPI, in which the alginate composes the matrix material and the PVPI is the dispersed phase.

Within the scope of the invention, alginate can be used in the form of soluble alginate, such as, for example, sodium or potassium alginate, or in the form of cross-linked, water-insoluble alginate, such as calcium alginate.

In general, the composite material that is the subject-matter of the invention can be a preferably substantially anhydrous composition, comprising or consisting of 55-80% by weight of alginate and from 45% to 20% by weight of PVPI, preferably from 60% to 76% by weight of alginate and from 40% to 24% by weight of PVPI, or more preferably from 65% to 75% by weight of alginate and from 35% to 25% by weight of PVPI.

In an embodiment, the matrix material and the medical devices produced therewith consist essentially of alginate and PVPI in the weight ratios indicated above.

Preferably, the composite material does not comprise other polysaccharides beside alginate, and particularly polysaccharides, such as sucrose, forming liquid systems with PVPI and which can thus give rise to deteriorations, losses or infiltrations, optionally increasing the patient's glycemic index.

In this preferred embodiment, the composite material and the medical devices produced therewith are particularly useful for the treatment of diabetic ulcers and for diabetic patients, since alginate does not increase the diabetic conditions, but it is able to control and regulate them.

However, the composite material may comprise other substances that are suitable for altering the mechanical properties of the material, for use in the production of specific biomedical devices.

Particularly, the material may comprise plasticizers, particularly glycerol, proteins or peptides (for example, gelatin), essential oils, surfactants, polyethylene glycol or a combination thereof, suitable to confer to the composite material the appropriate mechanical properties necessary for the production of the medical devices of interest.

Particularly, self-supporting films, useful as a wound dressing, can be produced by using a composition comprising sodium alginate as a matrix material, PVPI as a dispersed material, and glycerol as a plasticizer.

Typically, the plasticizer, as well as any of the materials indicated above, can be comprised in the composition in amounts, for example from 5% to 35% by weight, referred to the total weight of the alginate/PVPI material, more preferably from 20% to 30% by weight.

For the production of medical devices, such as microcapsules for the release of PVPI and suture threads, it is preferable to use a cross-linked calcium alginate as a matrix material.

Films useful as a wound dressing, microcapsules ("beads") and suture threads can be obtained by the following preparative examples.

DETAILED DESCRIPTION OF THE PREFERRED EMBODIMENT

Figure 1:
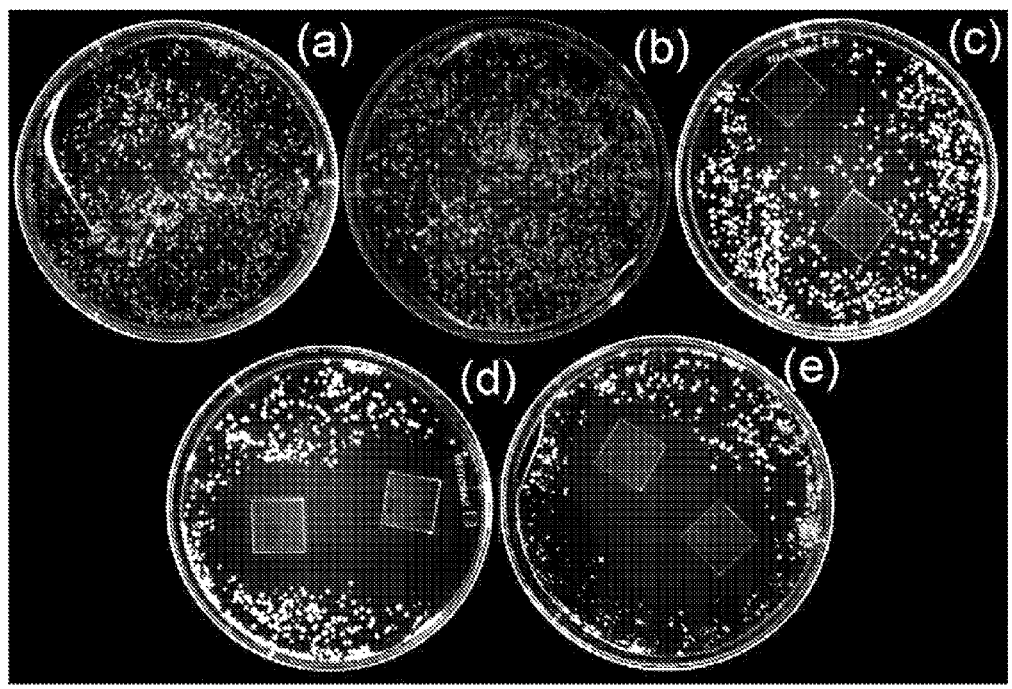
FIG. 1 shows photographies of films after 48 incubation with the following compositions: pure NaAlg (a); NaAlg 70%, 30% glycerol (plasticizer) film (b); NaAlg 57%, 25% glycerol, 18% PVPI film (c), 52% NaAlg, 22% glycerol, 26% PVPI (d), 48% NaAlg, 20% glycerol, 32% PVPI; two identical films were incubated in plastic Petri capsules containing *Candida albicans* fungi for all the experiments.

Example 1—Preparation of a Sodium Alginate/PVPI Film

For the preparation of the composites according to the invention, the following materials were prepared: alginic acid sodium salt having a viscosity of 15000-20000 cps, glycerol≥99.5 (GC) and anhydrous sodium chloride (all purchased from Sigma-Aldrich); 100 ml of PVPI solution in water containing 10% PVPI, 1% of which was active iodine purchased from Pharmatek PMC.

Three different NaAlg-PVPI films were produced to carry out antibacterial and antifungal tests. The films were prepared as follows: 10 ml distilled water with 0.3 g NaAlg were mixed and heated by using a hot plate during 1 hour up to about 100° C., to ensure the complete dissolution of alginate in water.

Next, the viscous solution was let to cool to room temperature, and 0.1 ml glycerol as the plasticizer was added. The amount of added glycerol was kept constant in all the successive preparations of the solution. Different volumes (1.0 ml, 1.5 ml, and 2.0 ml) of a PVPI aqueous solution were slowly mixed to the NaAlg/glycerol solutions.

The final solutions were mixed by using a Vortex mixer and left to rest for a period of time to ensure the absence of bubbles in the vials. By using a pipette, the prepared solutions were poured dropwise on substrates of 1 cm$^2$ and left at laboratory room temperature to dry.

According to the above-mentioned procedure, the following films were prepared:
film 1: 57% NaAlg, 25% glycerol, and 18% PVPI;
film 2: 52% NaAlg, 22% glycerol, and 26% PVPI;
film 3: 48% NaAlg, 20% glycerol, and 32% PVPI.

Percentages are expressed by weight.

Example 2—Preparation of Calcium Alginate Microcapsules ("Beads") and of Sutures Containing PVPI By way of example, the above-mentioned solution, which was used for the production of the film 3 (48% NaAlg, 20% glycerol, and 32% PVPI), was used for preparing CaAlg/PVPI beads and suture threads, respectively.

For the production of the beads, the NaAlg/PVPI solution was introduced by dipping dropwise or, respectively, for the production of suture threads, it was continuously supplied by a syringe in a 10% calcium chloride solution in distilled water. The formation of the beads and the suture threads was immediate; however, the so-obtained products were left in the calcium chloride solution during 30 minutes to ensure a high cross-linking.

Next, the thus-formed materials were rinsed with distilled water to ensure the complete removal of calcium chloride traces and let to dry overnight. The cross-linking time may be varied in order to obtain a higher or lower cross-linking, as a function of the desired application.

Example 3—Test to Assess the Antibacterial/Antimycotic Activity of Sodium Alginate/PVPI Films In these tests, the activity of NaAlg/PVPI films coated on slides against two different microorganisms, particularly, Gram-negative bacterium *E. Coli* and fungus *C. albicans* known as the agent responsible for oral and genital opportunistic infections in humans was tested. The above-mentioned coated slides, herein below referred to as substrates, were also tested with different concentrations of bacteria and fungi to better determine the antimicrobial characteristics thereof.

In order to verify the antibacterial properties of the sodium alginate/iodopovidone films, an *E. Coli* culture incubated overnight with a final concentration of 8×10$^8$ cells/ml was diluted to final concentration of 10$^6$ cells/ml, and 500 µL of this solution were deposited on a plate with fresh Luria-Bertani (LB) culture medium.

Subsequently, the plates were placed in an incubator at 37° C. for two hours (to allow the evaporation of the residual culture medium) and the different substrates (two for each LB plate) were placed. To assess the antifungal activity of the sodium alginate/iodopovidone films, the initial inoculum of 10$^8$ cells/ml was diluted to 10$^5$ cells, and 100 µL of this solution were deposited on a fresh Sabouraud dextrose agar (SDA) culture medium. Next, the plates were placed in the incubator at 37° C. for two hours and two different substrates were placed on each of them.

Analysis of the Antibacterial Activity of the Films

The sodium alginate/PVPI films with the following compositions (a) pure sodium alginate (b) 70% NaAlg, 30% glycerol (plasticizer); (c) 57% NaAlg, 25% glycerol, 18% PVPI; (d) 52% NaAlg, 22% glycerol, 26% PVPI; (e) 48% NaAlg, 20% glycerol, 32% PVPI were prepared and tested after 24 hours incubation; films with the following compositions were tested after 24 hours incubation: (f) 57% NaAlg, 25% glycerol, 18% PVPI; (g) 52% NaAlg, 22% glycerol, 26% PVPI and (h) 48% NaAlg, 20% glycerol, 32% PVPI.

At the end of the incubation period of 24 hours, the formation of a bacterial film on both coatings was observed. On the films containing 18% PVPI, the formation of a thin inhibition area free from bacteria without the formation of a bacterial biofilm upon or around the films was observed after 24 hours incubation.

Similarly, for those films containing 26% and 32% of the PVPI complexes, no growth upon or around the films was detected after 24 hours, with the formation of inhibition areas around the films. Samples were incubated during 48 hours to study the longevity of the antibacterial effect obtained after 24 hours. For films containing 18%, 26%, and 32% PVPI complexes, no bacterial growth was observed upon or around the films without significant changes of the inhibition areas around them.

The PVPI complex is very active even when it is incorporated in the NaAlg matrix. Furthermore, the formation of an inhibition area around all the films containing PVPI complexes indicates that PVPI is released from the NaAlg matrix, thus making these compounds not only surface active, but also inhibitory.

Analysis of the Antimycotic Activity of Sodium Alginate/PVPI Films

With reference to the activity of the prepared films against *Candida albicans*, after 24 hours incubation, it was observed that the control samples comprising pure sodium alginate and 70% NaAlg, 30% glycerol did not show any antifungal activity. In fact, a growth of fungi *Candida albicans* is noticed upon and about the substrates. However, when the samples containing the PVPI complex were incubated, no growth was detected upon and around the films. Furthermore, it was observed that there was drug release during the incubation process, since *Candida albicans* was not able to grow not even in those regions far from the films, due to the formation of a large inhibition region.

Similar results were obtained after 48 hours incubation of the NaAlg/PVPI films.

Films of pure NaAlg and glycerol-plastified NaAlg were both invaded by the fungi, as seen in FIGS. 1 (*a*) and 1 (*b*), while the films containing the PVPI complex show areas on the surface thereof that are free from fungi, as well as a large inhibition area around them, as shown in FIGS. 1 (*c*), 1 (*d*), and 1 (*e*).

Experimental tests carried out with NaAlg/PVPI films show a higher efficiency against *Candida albicans* fungi than against *E. coli* bacteria, creating larger inhibition areas around the coated films.

Example 4—Test for Verifying the Antibacterial/Antifungal Activity of Calcium Alginate/PVPI Beads Microcapsules of calcium alginate/PVPI obtained according to the procedure of the example 2 by depositing droplets of NaAlg/PVPI aqueous solutions in a container containing an excess of $CaCl_2$ dissolved in water were tested for their antibacterial and antimycotic activity. The obtained beads have an average dimension of about 3 mm. The calcium alginate beads allow the complete encapsulation of the PVPI complex in water, while the same amount of PVPI complex is immediately released in water after the dropwise addition.

The antibacterial/antimycotic properties of the calcium alginate/iodopovidone beads were tested by a turbidity assay. Particularly, a *C. albicans* culture incubated overnight and which reached confluence was diluted to an $OD_{600}$ of 0.1, then 1 g of calcium alginate/PVPI beads was added to the culture, and the optical density at 600 nm was measured every 30 minutes with a spectrophotometer (Thermo Scientific).

The same turbidity assay was performed with *E. coli*, but, in this case, 12 g of calcium alginate beads were added to the bacterial culture.

Figure 2:
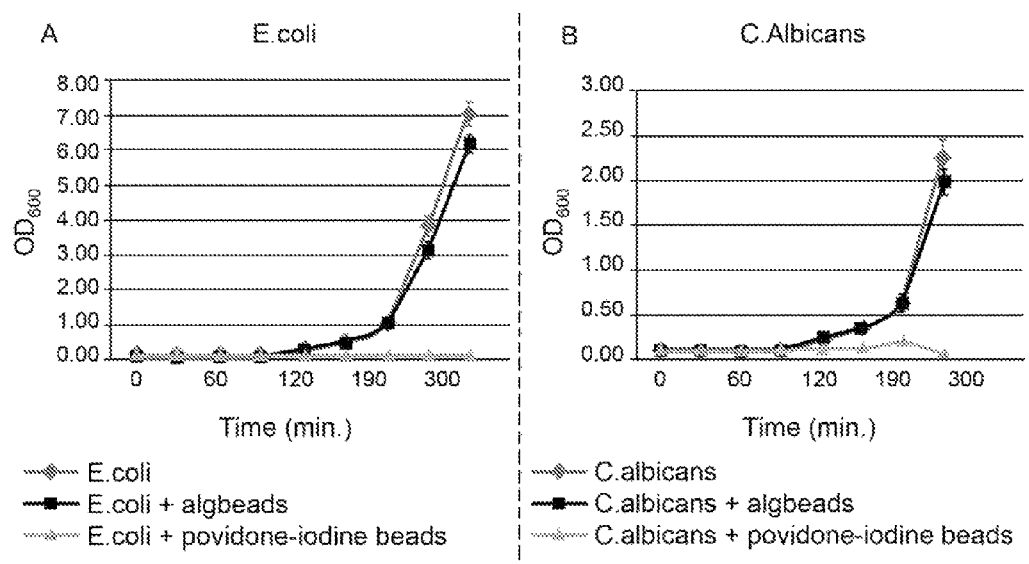
FIG. 2 shows in the box (A) the growth curves for *E. coli* in water (line with rhombi), in water containing beads of CaAlg (line with squares), in water containing beads of CaAlg/PVPI (line with triangles); in the box (B), the growth curves for *C. albicans* in the presence of sodium alginate beads (line with squares), and iodopovidone beads (line with triangles) are shown.

As shown by the results in FIG. 2A, the growth curves of fungi *C. albicans* which contacted the aqueous solution containing 1 g of CaAlg beads are similar to those of the control, consisting in water only. On the contrary, the curve relative to fungi growing with 1 g of calcium alginate/iodopovidone beads shows that the cell population never starts to grow, thus indicating the cell death. The same results were obtained with *E. coli* cultures as shown in FIG. 2B, but a higher amount of sodium alginate/iodopovidone beads, i.e., 12 g, was necessary to stop the bacterial growth. This is because the minimum bactericidal concentration of $2 \times 10^{-3}$ M iodopovidone was higher than the respective minimum fungicidal concentration of $1 \times 10^{-3}$ M.

Quantification of PVPI Release from Calcium Alginate/PVPI Beads

The dynamic release of PVPI from calcium alginate beads was measured by dipping a different number of freshly prepared beads corresponding to 1 g and 8 g in water, then monitoring absorbance at $\lambda = 360$ nm at time intervals of 5 minutes. In this manner, the amount of PVPI encapsulated in the beads is calculated, then the amount thereof that is necessary to reach the minimum bactericidal concentration (MCB) and the minimum fungicidal concentration (MFC) of PVPI within each culture is calculated.

Figure 3:
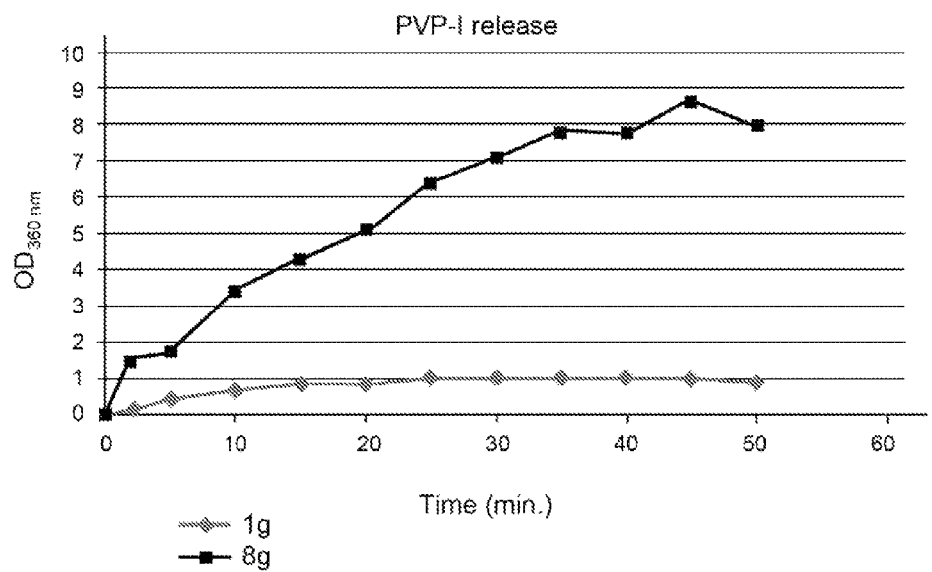
FIG. 3 is a dynamic release scheme for 1 g PVPI (line with rhombi) and from 8 g (line with squares) of calcium alginate beads in water; PVPI release is quicker (within 15 minutes) in the solution containing 1 g of beads than that containing 8 g.

As shown in FIG. 3, the release from the solution containing 1 g of beads reaches more quickly the release plateau (within 25 minutes) compared to a solution containing 8 g of CaAlg/PVPI beads.

Furthermore, by constructing a calibration curve of PVPI in water, it was possible to quantify the amount of drug within the beads. Particularly, 1 g of beads contains about $1.7 \times 10^{-4}$ M PVPI, while 8 g of beads incorporate about $1.4 \times 10^{-3}$ M PVPI. This element, in association with the data for MBC and MFC, allowed calculating the amount of CaAlg/PVPI beads necessary to stop the growth of *C. albicans* and *E. coli* corresponding to 1 g and 12 g, respectively.

The controlled release characteristics of the beads, combined with the antiseptic properties, biocompatibility and biodegradability thereof, make such beads particularly suitable in clinical applications as internal and external antiseptic fillers for wounds, and do not require removal interventions.

The threads obtained by the procedure of the example 3 can be used as suture threads for surgical sutures. By virtue of the incorporation of PVPI in the alginate matrix, such sutures have antimicrobial properties suitable to significantly reduce the infection risk of the wound after surgery.

Furthermore, since such sutures are also biodegradable, they are ideal for those patients who do not need to be re-hospitalized for suture removal. Biodegradation times turn out to be sufficient to allow healing, while maintaining the required bonding function.

Furthermore, the described composite materials find application as antimicrobial coatings, or as packaging materials for food and biomedical industries, as well as acting as purification and sterilization materials against bacterial contaminations.

LEGENDA

Time=tempo
Release=rilascio

The invention claimed is:

1. A medical device with antiseptic action, configured as a self-supporting film comprising a matrix of water soluble alginate in which a complex of povidone-iodine (PVPI) is dispersed as an antiseptic agent, said self-supporting film being a substantially anhydrous composition consisting of said water soluble alginate, said complex of povidone iodine, and a plasticizer; wherein said water soluble alginate is present in an amount of 55% to 80% by weight, and said povidone iodine is present in an amount of 45% to 20% by weight, wherein the amount percentages are relative to a total amount of said alginate and povidone-iodine, and wherein said plasticizer is present in an amount of 20% to 35% by weight relative to the total amount of said alginate and povidone-iodine.

2. The medical device according to claim 1, wherein the matrix is sodium alginate or potassium alginate.

3. The medical device according to claim 1, configured as a film, having antiseptic activity and adapted for the release of PVPI.

4. The medical device according to claim 1, the device consisting of
   48% wt-57% wt sodium alginate;
   20% wt-25% wt glycerol; and
   18% wt-32% wt PVPI;
   wherein the amounts of sodium alginate, glycerol and PVPI add up to 100%.

5. The medical device according to claim 1, wherein said self-supporting film is obtained by mixing sodium alginate in water, heating to about 100° C., to ensure complete dissolution of the alginate in water, cooling to room temperature, adding said plasticizer, further adding a PVPI aqueous solution, pouring dropwise the obtained solution on a substrate and maintaining at room temperature to dry.

* * * * *